United States Patent [19]

Cherry et al.

[11] 4,230,622

[45] Oct. 28, 1980

[54] HALOGEN DERIVATIVES OF CLAVULAIC ACID

[75] Inventors: Peter C. Cherry, Aylesbury; Gordon I. Gregory, Chalfont St. Peter; Peter Ward, Northolt, all of England

[73] Assignee: Glaxo Laboratories Limited, Greenford, England

[21] Appl. No.: 749,368

[22] Filed: Dec. 10, 1976

[30] Foreign Application Priority Data

Dec. 17, 1975 [GB] United Kingdom ............... 51689/75
Jun. 25, 1976 [GB] United Kingdom ............... 26594/76

[51] Int. Cl.³ .......................................... E07D 498/04
[52] U.S. Cl. ................................. 260/245.3; 546/272
[58] Field of Search ..................... 260/307 FA, 245.3; 546/272

[56] References Cited

PUBLICATIONS

Cram et al. "Organic Chemistry" 2nd Ed., McGraw-Hill, N.Y. (1964) pp. 258–259.

*Primary Examiner*—Donald G. Daus
*Assistant Examiner*—D. B. Springer
*Attorney, Agent, or Firm*—Bacon & Thomas

[57] ABSTRACT

Novel halogen derivatives of clavulanic acid are described which are of value in the preparation of a range of clavulins which either inhibit β-lactamases or show activity against strains of both gram-positive and gram-negative bacteria. Processes for preparing the halogen derivatives are described and methods for converting them into the active clavulins are given.

6 Claims, No Drawings

HALOGEN DERIVATIVES OF CLAVULAIC ACID

This invention relates to novel antibiotic intermediates and to a process for their preparation.

In our German OLS No. 2,604,697 we have described the isolation, from fermentations of *Streptomyces clavuligerus*, of the carboxylic acid having the formula (I) (clavulanic acid)

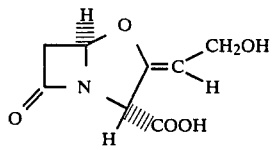

and salts thereof in pure form. The compounds in this specification are named with reference to "clavam"; the name given to the parent heterocycle of formula A

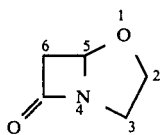

by analogy with the term "cepham" used in the naming of cephalosporin compounds in J. Amer. Chem. Soc., 1962, 84, 3400. Thus the compound of formula (I) is named (3R, 5R, Z)-2-(2-hydroxyethylidene)clavam-3-carboxylic acid.

The present invention is concerned with new compounds having the formula

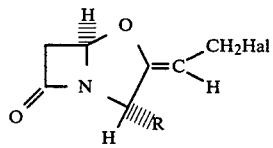

wherein R represents an esterified carboxyl group, and Hal represents a chlorine, bromine or iodine atom.

The above esters constitute one feature of the present invention.

The compounds of the invention are of use, as detailed below, as intermediates in the preparation of antibiotic acids and their esters, for example derivatives in which the halogen atom is replaced by, for example, a hydrogen atom to form an ethylidene compound, or by the residue of a sulphur nucleophile. These derivatives of the acid of formula I and their esters generally possess the ability to inhibit β-lactamase enzymes, for example, those produced by gram-positive organisms, e.g. those produced by *Staphylococcus aureus* and the enzymes classified in classes II-V (as described in Advances in Microbial Physiology 9, 31–88) from gram-negative bacteria produced by such organisms as *Proteus micrabilis, Escherichia coli, Proteus morganii, Klebsiella aerogenes, Salmonella typhimurium* and *Haemophilus influenzae* and are useful in combination with β-lactam antibiotics susceptible to β-lactamase hydrolysis, e.g. ampicillin, cephalexin etc., and in the case of the ester derivatives, are useful as carboxyl protected intermediates. In addition, these derivatives in the form of their acids and salts and metabolically labile esters show antibacterial activity against strains of both gram-negative and gram-positive bacteria.

Haloesters of the invention may be converted into the above-described ethylidene compounds by reduction e.g. by hydrogenolysis, for example using a metal catalyst, e.g. a noble metal catalyst such as palladium, platinum or rhodium. The catalyst may be supported, e.g. on charcoal or kieselguhr.

Using an amount of catalyst in excess of that needed merely to sustain reaction at a moderate rate, a brisk reaction occurs and the yield of product is optimised, Using these higher ratios of catalyst to substrate, hydrogenolysis occurs rapidly at ambient temperature and pressure and uptake of hydrogen ceases after a short time. The noble metal is preferably palladium. Hydrogenolysis will desirably be effected in an organic solvent e.g. an ester solvent such as ethyl or butyl acetate, an alkanol solvent such as methanol, ethanol or butanol, a ketone solvent such as acetone or an ether solvent such as tetrahydrofuran.

Where a starting ester is employed which is cleaved by catalytic hydrogenation, the free acid will be formed and this may be isolated from the reaction solution by formation of a salt thereof, for example, an alkali metal, e.g. sodium or potassium, salt using a suitable base, for example, an alkali metal alkanoate e.g. sodium 2-ethyl hexamate. It may be necessary to precipitate the salt of the acid by addition of a precipitant such as diethyl ether or sec-butanol. The free acid may be liberated from the salt and esterified if desired by methods described below.

An additional and important utility of the halo compounds of the invention is their ability to react with sulphur nucleophiles to yield compounds wherein the halogen atom is replaced by the S-attached residue of the sulphur nucleophile. Such sulphur compounds have shown antibacterial and β-lactamase inhibitory action as described above. The sulphur derivatives may, in general, be obtained from a halo-ester according to the present invention by reaction with the sulphur nucleophile or a salt thereof, if desired in the presence of an acid binding agent.

In general, we have found the bromo-derivatives according to the present invention to react more readily with sulphur nucleophiles than do the corresponding chloro-compounds. Thus, for example, reaction with methane thiol using silver nitrate to assist removal of halogen, results in substantially higher yields of methylthio product where a bromo-ester according to the invention is used, as compared with a corresponding chloro-ester.

Furthermore, in the case of the p-nitrobenzyl esters the chloro-ester is relatively insoluble in organic solvents, whereas the corresponding bromo compound is soluble in ester solvents such as ethyl acetate, ether solvents such as tetrahydrofuran, nitrile solvents such as acetonitrile and substituted amide solvents such as dimethylformamide; such solubility naturally facilitates use of the bromo compound as an intermediate.

On the other hand, the chloro compounds may be prepared using cheaper reagents than the bromo compounds and may be advantageous in this respect.

During the preparation of the halo compounds, mixtures of Z- and E-isomers are formed, the Z-isomers of formula II being the major component. The present invention also extends to the E-isomers of the compounds of the formula II, and to mixtures thereof with the Z-isomers. The chloro and bromo compounds of the invention in the form of their p-nitrobenzyl esters crystallise in the Z-isomeric form, leaving any E-isomer in solution thereby effecting ready separation of the two isomers. The p-nitrobenzyl ester of the Z-isomer of the chloro-compound crystallises particularly readily, e.g. from ether solvents, and may obtained in substantially complete isomeric purity.

The esters of the invention i.e. compounds wherein R represents an esterified carboxyl grop COOR$^1$ will in general be derived from aliphatic orr araliphatic alcohols, phenols or stannonols preferably containing not more than 24 carbon atoms. The esterifying group R$^1$ may thus, for exxample, be:

a straight or branched, substituted or unsubstituted alkyl or alkenyl group, preferably having up to 8 carbon atoms, for example a methyl, ethyl, propyl, isopropyl, butyl, sec-butyl, tert-butyl or allyl group, desirable substituents being, for example, alkoxy e.g. methoxy; halogen i.e. fluorine, chlorine, bromine or iodine; cyano; acyloxy e.g. alkanoyloxy such as acetoxy or pivaloyloxy; acyl e.g. p-bromobenzoyl and carboalkoxy, e.g. carboethoxy;

an aralkyl group having up to 20 carbon atoms especially an arylmethyl group e.g. a benzyl or substituted benzyl group, suitable ring substituents being halo e.g. chloro; nitro eg o- or p-nitro; sulphonyl; cyano; alkyl e.g. p-methyl or alkoxy e.g. p-methoxy; a diphenylmethyl, or triphenylmethyl group or a fur-2-ylmethyl, thien-2-ylmethyl or pyrid-4-ylmethyl group. The heterocyclic groups of which may also be substituted e.g. by a lower alkyl group, preferably methyl;

an aryl group having up to 12 carbon atoms e.g. a phenyl or substituted phenyl group, suitable substituents being halo e.g. chloro; nitro e.g. o- or p-nitro; cyano; alkyl e.g. p-methyl or alkoxy e.g. p-methoxy;

a cycloalkyl group containing not more than 12 carbon atoms, e.g. adamantyl;

a heterocyclic group containing not more than 12 carbon atoms, the heteroatom being for example oxygen, as in the tetrahydropyranyl or phthalidyl groups;

or a stannyl group having up to 24 carbon atoms, for example a stannyl group carrying three substituents which may be the same or different selected from alkyl, alkenyl, aryl, aralkyl, cycloalkyl, alkoxy, aryloxy or aralkoxy groups. Such groups will include methyl, ethyl, propyl, n-butyl, phenyl and benzyl groups.

In general, the most preferred esters of the invention are the substituted and unsubstituted aralkyl esters for example the p-nitrobenzyl, diphenylmethyl and benzyl esters.

In general, the chloro and bromo compounds of the invention are most preferred, especially in the form of their p-nitrobenzyl esters.

As mentioned above, esters according to the invention are capable of yielding the above-described ethylidene or sulphur compounds which have in general β-lactamase inhibitory action. Some of the esters according to the invention which are readily convertible to carboxylic acids, for example by reduction and/or hydrolysis, notably the p-nitrobenzyl, diphenylmethyl and benzyl esters, are also useful as carboxyl-protected intermediates in the production of the above ethylidene and sulphur derivatives as their acids and salts.

The esters of the compounds of formula II may be prepared, for example, by reaction of esters of the acid of formula I with one or more reagents serving to replace the allylic hydroxy group by chlorine, bromine or iodine.

The halogenating agent will most desirably be a non-metallic halide containing at least one covalently bound halogen atom and which readily effects the conversion of an allylic hydroxyl compound to the corresponding halo compound.

The halogenating agent may have the formula XAY where A is selected from SO, POX, or PX and X and Y are chlorine or bromine or A is SO$_2$, X is chlorine or bromine, and Y is an alkyl or aryl group, the reaction in the latter case being carried out in the presence of halide ions.

In a preferred embodiment, the halogenating agent will be phosphorus trichloride or phosphorus tribromide; or thionyl chloride or bromide. Thionyl chloride or bromide is preferred. The reaction is preferably effected in the presence of a mild inert base for example a pyridine base e.g. pyridine itself or collidine. A solvent will normally be present e.g. an ether such as diethyl ether or tetrahydrofuran, an ester such as ethyl or butyl acetate, a substituted amide such as dimethylformamide, dimethylacetamide or hexamethylphosphoramide or a substituted sulphoxide such as dimethylsulphoxide. The reaction temperature is preferably low, e.g. −70° to +5° C., for example about −60° to 0° C.

Alternatively the halogenating agent may be a hydrocarbon sulphonyl halide conveniently used in the presence of a source of halide ions. The hydrocarbon sulphonyl halide may, for example, be an alkane sulphonyl halide such as a methanesulphonyl halide, or an aryl sulphonyl halide such as a p-toluene sulphonyl halide. The sulphonyl halide will in general be a chloride or bromide, methane sulphonyl chloride being preferred. This reaction is normally carried out in a solvent system similar to that described above, an amide solvent being preferred. The source of halide ions will be a halide salt soluble in the medium and may, for example, be a lithium halide or a tertiary or quaternary amine salt, e.g. a triethylamine, trimethylamine, pyridine or collidine hydrohalide or a tetrabutyl ammonium halide. A mild inert base is preferably present to take up eliminated hydrohalic acid, e.g. a pyridine base such as pyridine itself or collidine. In general, the halide salt should provide the same halide ions as the hydrocarbon sulphonyl halide. The reaction temperature is preferably low, e.g. −40° to +5° 1 C. for example about −5° to −10° C.

In the above reaction, it is thought that a hydrocarbylsulphonyloxy group is introduced initially and is then displaced by halide ion.

Owing to the high chemical reactivity of the product of formula (II) it is desirable that the halogenation reaction be carried out under mild conditions in order to obtain optimum yields and to avoid undesirable side-reactions.

The above methods are of use in preparing the chlorides and bromides according to the invention. The corresponding iodides may be formed by a halogen exchange reaction, for example by reacting a chloride or bromide ester formed by the above procedure with a source of iodide ions e.g. sodium or lithium iodide or a tertiary or quaternary ammonium iodide, conveniently in an ether solvent e.g. tetrahydrofuran, a ketone solvent such as acetone or an amide solvent such as dimethylformamide. It may be desirable, in view of the reactivity of the novel intermediates of formula (II), to react them in situ with further reagents so as to avoid the need to isolate them. This is especially so in the case of the iodine compounds, which are extremely reactive and so these are desirably prepared and employed directly in situ.

The starting material for the above halogenation reaction is an ester of the acid of formula I. This may be prepared in the conventional way. Thus for example, a salt of the acid of formula I may be reacted with an alcohol, phenol or stannanol or a reactive derivative thereof e.g. a halide to form the desired ester. Reaction will desirably be effected under mild conditions in order to prevent rupture of the bicyclic nucleus. The use of neutral or mild acidic or basic conditions, therefore at temperatures between −70° C. and +35° C. is preferred.

The alkyl, alkoxyalkyl and aralkyl esters may be prepared by reaction of the acid of formula I with the appropriate diazoalkane or diazo-aralkane e.g. diazomethane or diphenyldiazomethane. The reaction will generally be effected in an ether, ester, alkanol or halohydrocarbon solvent, e.g. diethyl ether, ethyl acetate, methanol, ethanol or dichloromethane. In general, reduced temperatures are preferred, for example −15° C. to +15° C.

The esters derived from alcohols may be produced by reaction of a reactive derivative of the alcohol, for example, a halide such as the chloride, bromide or iodide, or a hydrocarbonsulphonyl derivative such as a mesyl or tosyl ester, with a salt of the acid of formula I, e.g. an alkali or alkaline earth metal salt such as a lithium, sodium, potassium, calcium or barium salt or an amine salt such as a triethylammonium salt. This reaction is preferably carried out in a substituted sulphoxide or amide solvent e.g. dimethyl sulphoxide, dimethylformamide or hexamethylphosphoramide.

Stannyl esters may conveniently be formed by reaction of the carboxylic acid of formula I or a salt thereof with tin compounds having reactive tetravalent tin moieties. Trialkyl tin oxides are preferred for the synthesis of stannyl esters in view of their availability and low toxicity.

The invention will now be more particularly described in the following Preparations and Examples, which should not be understood as limiting the invention.

PREPARATION 1

4-Nitrobenzyl(3R,5R,Z)-2-(2-hydroxyethylidene)-clavam-3-carboxylate

A mixture of lithium (3R,5R,Z)-2-(2-hydroxyethylidene)-clavam-3-carboxylate (10 g.) prepared as in our German OLS No. 2,604,697, 4-nitrobenzyl bromide (9.5 g.) and hexamethyl-phosphoramide (65 ml) was stirred for 18 hr. at room temperature. The suspension was then partitioned between ethyl acetate (800 ml.) and 50% saturated aqueous sodium chloride solution (800 ml). The organic layer was separated, washed successively with water, 0.5 M aqueous sodium hydrogen carbonate solution and water, dried and concentrated to a slurry and the colourless crystals collected to give the title ester (8.39 g.), m.p. 117.2° (Mettler, $\lambda_{max}^{EtOH}$ 264 nm ($\epsilon$ 11,000), $\nu_{max}$ (CHBr$_3$) 1781 ($\beta$-lactam), 1738 (ester), 1680 cm$^{-1}$ (O—C=C), $\tau$ (CDCl$_3$) values include 4.30 (d, J 2 Hz, C-5H), 4.61 (s, benzylic protons), 5.09 (t, J 7 Hz, =CH—) and 5.78 (d, J 7 Hz, —CH$_2$OH).

PREPARATION 2

Diphenylmethyl(3R,5R,Z)-2-(2-hydroxyethylidene)-clavam-3-carboxylate

To a suspension of lithium (3R,5R,Z)-2-(2-hydroxyethylidene)-clavam-3-carboxylate (3.075 g.) in ethyl acetate (150 ml) and brine (20 ml) was added 2 N hydrochloric acid (25 ml). The mixture was quickly shaken and the organic layer separated. The aqueous layer was extracted once with ethyl acetate (35 ml). The combined organic extracts were dried over magnesium sulphate and concentrated in vacuo at below 20° to ca. 30 ml. To this stirred solution was added dropwise a concentrated solution of diphenyldiazomethane (1.94 g.) in methylene chloride (4 ml). The resulting solution was concentrated in vacuo to an oil, which was chromatographed on a column of silica gel, eluting with ether:-light petroleum (40°-60°) (1:1) followed by ether. The appropriate fractions were combined and the solvent evaporated to yield the title ester as a colourless crystalline solid (3.033 g.) m.p. 82.9° (from ether). $\nu_{max}$ (Nujol) 3420 cm$^{-1}$ (OH), 1800 cm$^{-1}$ ($\beta$-lactam), 1740 cm$^{-1}$ (ester), 1692 cm$^{-1}$ (O—C=C). $\tau$(CDCl$_3$) values 2.66 (s, aromatics), 3.08 (s, —CH(C$_6$H$_5$)$_2$), 4.30 (d, J 3 Hz, C-5H), 4.86 (s, C-3H), 5.14 (t, J 6 Hz =CH—), 5.82 (d, J 6 Hz, —CH$_2$OH), 6.52 (dd, J 17 and 3 Hz, C-6$\alpha$H), 6.96 (d, J 17 Hz, C-6$\beta$H), 8.48 (s, —OH).

PREPARATION 3

Benzyl(3R,5R,Z)-2-(2-hydroxyethylidene)clavam-3-carboxylate

A mixture of lithium (3R,5R,Z)-2-(2-hydroxyethylidene)clavam-3-carboxylate (10.25 g) and benzyl bromide (8.55 g) in hexamethylphosphoramide (50 ml) was stirred at room temperature for 22 hrs. The mixture was then diluted with ethylacetate (1 l.) and washed successively with 50% saturated brine (1 l.), water (2×500 ml) 5 M NaHCO$_3$ (500 ml) and brine (3×250 ml). The organic layer was dried (Na$_2$SO$_4$) and concentrated in vacuo to an oil, which was chromatographed on a column of silica gel (150 g) and eluted with chloroform followed by ethyl acetate. The appropriate fractions were combined and concentrated in vacuo to yield the title ester (8.8 g) as an oil, $\nu_{max}$ (CHBr) 3590 (—OH), 1786 ($\beta$-lactam), 1732 (ester), 1684 (—O—C=CH), 734 cm$^{-1}$ (phenyl). $\tau$ (CDCl$_3$) 2.68 (s, phenyl), 4.38 (d, J 3 Hz, C-5 H), 4.85 (s, CH$_{-2}$Ph), 4.95 (s, C-3H), 5.16 (t, J 7 Hz, =CH), 5.85 (d, J 7 HZ, —CH$_2$ OH), 6.55 (dd, J 17 and 3 Hz, C-6$\alpha$H), 6.98 (d, J 17 Hz, C-6$\beta$H), 8.29 (s, —CH$_2$OH).

EXAMPLE 1

4-Nitrobenzyl(3R,5R,Z,)-2-(2-chloroethylidene)-clavam-3-carboxylate

A solution of 4-nitrobenzyl(3R,5R,Z)-2-(2-hydroxyethylidene)-clavam-3-carboxylate (1.0 g.) in ethyl acetate (20 ml.) containing pyridine (0.32 ml.) was cooled to −60° stirred and treated with a solution of thionyl chloride (0.26 ml.) in ether (2.0 ml.). The mixture was warmed to −10° and stirred for a further 10 min. at −10° to 0° and then diluted with ether (250 ml.). The mixture was washed successively with 0.5 N aqueous hydrochloric acid, water, saturated aqueous sodium hydrogen carbonate solution (until the washings were colourless) and water. The ether layer was dried and concentrated to give a slurry of colourless needles which were collected by filtration, washed with ether and dried to give the chloro ester (320 mg.), $[\alpha]_D +30°$ (c, 0.49, DMSO) $\lambda_{max}^{EtOH}$ 264 nm ($\epsilon$ 10,550), $\nu_{max}$ (CHBr$_3$) 1800 ($\beta$-lactam), 1753 (ester), 1692 cm$^{-1}$ (O—C=C), $\tau$ (CDCl$_3$) values include 4.25 (d, J 2 Hz, C-5H), 4.7 (s, benzylic protons), 5.08 (t, J 8 Hz, =CH—), 5.82 (d, J 8 Hz, CH$_2$Cl).

EXAMPLE 2

4-Nitrobenzyl(3R,5R,Z)-2-(2-chloroethylidene)-clavam-3-carboxylate

A solution of 4-nitrobenzyl(3R,5R,Z)-2-(2-hydroxyethylidene)-clavam-3-carboxylate 1 g.) and lithium chloride (254 mg.) in dimethylformamide (10 ml.) and collidine (0.88 ml.) was cooled to $-10°$ stirred and treated dropwise with methanesulphonyl chloride (0.52 ml.). The mixture was stirred for 1.25 hr. at $-10°$ to $-5°$ and then diluted with ether (15 ml.) and the resulting suspension was partitioned between ether and saturated aqueous cupric nitrate solution. The ether layer was washed with water, filtered through a bed of sodium sulphate and evaporated to dryness. The residual gummy solid was triturated with ether to give a pale yellow granular solid which was collected by filtration, washed with ether, and dried in vacuo to afford the crude title ester (450 mg.). The crude product was extracted with dichloromethane (25 ml.) and the extract charcoaled and concentrated to ca. 2 ml., when the product began to separate as colourless needles. Crystallisation was maximised by addition of ether and the pale yellow solid collected, washed with ether and dried in vacuo to afford the title ester (187 mg.) which had spectral and physical characteristics similar to those of Example 1.

EXAMPLE 3

Sodium(3R,5R,Z)-2-ethylidene-clavam-3-carboxylate

A solution of 4-nitrobenzyl(3R,5R,Z)-2-(2-chloroethylidene)-clavam-3-carboxylate (1.11 g.) in ethyl acetate (100 ml.) was hydrogenated over a 10% palladium on carbon catalyst (1 g.) at ambient temperature and atmospheric pressure. After 20 minutes, when uptake of hydrogen had ceased, the suspension was degassed, filtered through kieselguhr, and treated with a 1.0 M solution of sodium 2-ethylhexanoate in ethyl acetate (3 ml.). The solution was then concentrated in vacuo to ca. 50 ml., and the resulting syrupy liquid diluted slowly with ether (100 ml.) followed by petrol (b.p. 40°–60°), (20 ml.). The resulting precipitate was collected, washed with ether and dried in vacuo to give the title salt containing less than 10% of the corresponding E-isomer (0.509 g.), $[\alpha]_D +69°$ (c, 0.99 water), $\lambda_{max.}^{0.1\,M\,NaOH}$ 257.5 nm ($\epsilon$ 13,930), $\nu_{max}$ (Nujol) 1788 ($\beta$-lactam), 1704 (O—C=C), 1614 cm$^{-1}$ (carboxylate) $\tau$ (D$_2$O) values include 4.33 (d, J 3 Hz, C-5H), 5.22 (q, J 7 Hz, =CH—), and 8.42 (dd, J 7 and 1 Hz, —CH$_3$).

EXAMPLE 4

4-Nitrobenzyl(3R,5R,Z)-2-(2-bromoethylidene)-clavam-3-carboxylate

A stirred solution of 4-nitrobenzyl(3R,5R,Z)-2-(2-hydroxyethylidene)-clavam-3-carboxylate (10.0 g.) in a mixture of tetrahydrofuran (40 ml.), ethyl acetate (40 ml.), diethyl ether (50 ml.) and pyridine (4.0 ml.), cooled to $-60°$ under nitrogen was treated with a solution of thionyl bromide (3.7 ml.) in diethyl ether (25 ml.). After a rapid rise in temperature to $-25°$, the resulting suspension was cooled to $-40°$ and stirred at this temperature for 10 minutes. The mixture was then poured into a mixture of ether (2 liters) and water (1.5 liters), and, after thorough agitation, a white solid which floated in the aqueous layer was collected by filtration, washed with ether, and dried in vacuo over phosphorus pentoxide to afford the title ester as an off-white microcrystalline solid (5.9 g.), $\lambda_{max}$ (Nujol) 1792 ($\beta$-lactam), 1752 (ester), 1682 (O—C=C), 1518 and 1342 cm$^{-1}$ (NO$_2$). This sample contained a small amount of the corresponding E-isomer ($<10\%$) as indicated by reaction with 4-mercaptopyridine followed by t.l.c. analysis of the isomeric p-nitrobenzyl (3R,5R)-2-[2-(pyrid-4-ylthio)ethylidene]clavam-3-carboxylates.

The organic layer was washed successively with water ($2 \times 500$ ml.), aqueous pH 7 buffer ($2 \times 250$ ml.) and brine (500 ml.), and then dried over sodium sulphate, filtered, and concentrated under reduced pressure to give a slurry of crystalline solid. The solid was collected by filtration, washed with ether, and dried in vacuo to afford a second crop of the title ester (3.0 g.), $\lambda_{max}$ (Nujol) 1790 ($\beta$-lactam), 1752 (ester), 1682 (O—C=C), 1518 and 1342 cm$^{-1}$ (NO$_2$). This sample contained the corresponding E-isomer (ca. 25%) as indicated by reaction with 4-mercaptopyridine followed by n.m.r. analysis of the isomeric 4-nitrobenzyl (3R,5R)-2-[2-(pyrid-4-ylthio)ethylidene]clavam-3-carboxylates.

EXAMPLE 5

Reaction of 4-mercaptopyridine with 4-nitrobenzyl(3R,5R)-2-(2-bromoethylidene)-clavam-3-carboxylate A solution of 4-mercaptopyridine(133 mg.) in N,N-dimethylformamide (3.0 ml.) containing pyridine (47.5 mg.) was added with stirring at room temperature to 4-nitrobenzyl (3R,5R)-2-(2-bromoethylidene)-clavam-3-carboxylate (119 mg; a mixture of E- and Z-isomers obtained as the second crop in the previous example). The resulting solution was allowed to stand for 15 minutes, and then partitioned between ethyl acetate and water. The ethyl acetate layer was washed three times with water, dried over sodium sulphate, treated with charcoal, filtered through Kieselguhr and evaporated in vacuo to afford a mixture of Z- and E-isomers of 4-nitrobenzyl(3R,5R)-2-[2-(pyrid-4-ylthio)ethylidene]-clavam-3-carboxylate as a pale yellow gum (130 mg.), $\nu_{max}$ 1800 ($\beta$-lactam), 1755 (ester), 1695 cm$^{-1}$ (O—C=C), $\tau$ (CDCl$_3$) values (Z-isomer) include 4.18 (d, J 3 Hz, C-5H), 5.19 (t, J 7 Hz, =CH), 6.24 (d, J 7 Hz, CH$_2$—S), 6.36 (dd, J 17 and 3 Hz, C-6$\alpha$H), 6.88 (d, J 17 Hz, C-6$\beta$H). Additional closely associated resonances indicated the presence of the corresponding E-isomer (ca. 25%). Thin layer chromatography [silica gel, developed with ethyl acetate-toluene (3:3)] showed two spots, $R_f$ 0.5 and 0.4, of intensity ratio 1:3 respectively.

EXAMPLE 6

4-Nitrobenzyl(3R,5R,Z)-2-(2-methylthioethylidene)-clavam-3-carboxylate

4-Nitrobenzyl(3R,5R,Z)-2-(2-bromoethylidene)-clavam-3-carboxylate (2.8 g.) was added to a stirred ice-cold 10% w/w solution of methanethiol in acetonitrile (110 ml.), and the resulting solution treated immediately with pyridine (1.2 ml.) and then finely powdered silver nitrate (5.5 g.). The mixture was stirred rapidly at 0° for 25 minutes, and then filtered through Kieselguhr, washing the filter pad through with ethyl acetate (500 ml.). The filtrate and washings were concentrated under reduced pressure to ca. 300 ml. and then diluted to ca. 1 liter with ethyl acetate and washed with water (4×200 ml.). The organic layer was dried over sodium sulphate, filtered and concentrated under reduced pressure to ca. 20 ml. The concentrated solution was diluted to ca. 100 ml. with ether and chromatographed on a short column of silica gel (200 g.) eluting with ether. The eluate was evaporated in vacuo to leave the title ester as a pale yellow gum (2.3 g.), $\tau$ (CDCl$_3$) values include 4.26 (d, J 2 Hz, C-5H), 4.64 (s, benzylic protons), 4.80 (s, C-3H), 5.20 (t, J 7 Hz, =CH—), 6.24, (dd, J 2 and 17 Hz, C-6αH), 6.92 (d, J 17 Hz, C-6βH), 6.76 (d, J 7 Hz, CH$_2$—S) and 8.00 (s, S—CH$_3$).

EXAMPLE 7

Diphenylmethyl(3R,5R,Z)-2-(2-chloroethylidene)-clavam-3-carboxylate

A stirred solution of diphenylmethyl(3R,5R,Z)-2-(2-hydroxyethylidene)-clavam-3-carboxylate (730 mg.) and pyridine (237 mg.) in dry tetrahydrofuran (12 ml.) was cooled to −35° to −40° and treated with a solution of thionyl chloride (238 mg.) in ether (10 ml.). The temperature of the reaction rose to −15° and was then raised to 0°. The reaction mixture was stirred at this temperature for 10 minutes, and filtered to yield diphenylmethyl(3R,5R,Z)-2-(2-chloroethylidene)-clavam-3-carboxylate in the filtrate. This was characterised by adding to the filtrate ammonium dithiocarbamate (220 mg.) and the mixture stirred under nitrogen at room temperature for 5 minutes, then poured into ether (400 ml.) and washed with water (2×50 ml.) and pH 7 buffer solution (50 ml.). The organic layer was dried (MgSO$_4$) and the solvent evaporated in vacuo to yield diphenylmethyl(3R,5R,Z)-2-(2-thiocarbamoylthioethylidene)clavam-3-carboxylate as a crystalline solid, yield 808 mg, $\nu_{max}$ 3478, 3360 (NH$_2$), 1800 (β-lactam), 1748 (ester), 1690 (O—C=C) 750 cm$^{-1}$ (phenyl). $\tau$ (CDCl$_3$) values (Z-isomer) 2.67 (s, aromatic), 3.12 (s, —CH(C$_6$H$_5$)$_2$), 4.29 (d, J 3 Hz, C-5H), 4.84 (s, C-3H), 5.07 (t, J 7 Hz, =CH—), 6.08 (d, J 7 Hz, —CH$_2$—S—) 6.50 (dd, J 17 and 3 Hz, C-6αH), 6.94 (d, J 17 Hz, C-6βH). Additional closely associated resonances indicated the presence of the corresponding E-isomer (ca. 20%).

EXAMPLE 8

Benzyl(3R,5R,Z)-2-(2-chloroethylidene)-clavam-3-carboxylate

To a solution of benzyl(3R,5R,Z)-2-(2-hydroxyethylidene)-clavam-3-carboxylate (1.45 g.) in dry tetrahydrofuran (20 ml.) containing 0.474 g. of pyridine, cooled to −40° and stirred under nitrogen, was added thionyl chloride (0.708 g.) in ether (15 ml.). The temperature of the reaction rose to −10° C. and this was adjusted to 0° C. The mixture was stirred for 10 minutes then filtered to yield benzyl(3R,5R,Z)-2-(2-chloroethylidene))-clavam-3-carboxylate in the filtrate. This was characterised by addition to the filtrate of ammonium dithiocarbamate (0.550 g.) and the reaction mixture was stirred in an ice-bath for 7 minutes, diluted with ether (750 ml.) and washed with water (2×50 ml.) and brine (2×25 ml.) and dried (MgSO$_4$). Evaporation of the solvent yielded a foam (1.677 g.).

200 mg. of the crude product was purified by preparative layer chromatography on silica gel plates using ethyl acetate:light petroleum (40°–60° C.) (1:1) as eluant. The appropriate band was extracted with ethyl acetate and the solvent evaporated to yield benzyl (3R,5R,Z)-2(2-thiocarbamoylthioethylidene)clavam-3-carboxylate as an oil. (62 mg.) $\nu_{max}$ 3480, 3360 (NH$_2$) 1800 (β-lactam), 1748 (ester) 1690 cm$^{-1}$ (—O—C=C), $\tau$ values (CDCl$_3$) 2.63 (s, aromatic), 2.96 (s, —NH$_2$), 4.27 (d, J 3 Hz, C-5H), 4.79 (s, —CH$_2$Ph), 4.86 (s, C-3H), 5.08 (t, J 7 Hz, =CH), 6.09 (d, J 7 Hz, —CH$_2$S—), 6.48 (dd, J 17 and 3 Hz, C-6αH), 6.93 (d, J 17 Hz, C-6βH). Additional closely associated resonances indicated the presence of the corresponding E-isomer (ca. 25%).

EXAMPLE 9

4-Nitrobenzyl(3R,5R,Z)-2-(2-bromoethylidene)-clavam-3-carboxylate

A solution of 4-nitrobenzyl(3R,5R,Z)-2-(2-hydroxyethylidene)-clavam-3-carboxylate (1.00 g.) in dry tetrahydrofuran (10 ml.) and pyridine (1.02 ml.) was cooled to −70° under nitrogen and treated with a solution of phosphorus tribromide (0.105 ml.) in tetrahydrofuran (2.5 ml.). The resulting mixture was stirred at −40° for 10 minutes to afford a solution of the title ester which was characterised by reaction with 4-mercaptopyridine as follows:

The above solution was stirred at −40°, treated with a solution of 4-mercaptopyridine (1.33 g.) in N,N-dimethylformamide (11 ml.), and warmed to 20° for 15 minutes. The resulting solution was then partitioned between ethyl acetate and water, and the ethyl acetate layer separated, washed with water (3 times), dried over sodium sulphate, treated with charcoal, filtered through Kieselguhr and evaporated to leave a pale yellow gum (0.578 g.). The major component of the crude product was shown to be 4-nitrobenzyl (3R,5R,Z)-2-[2-(pyrid-4-ylthio)-ethylidene]clavam-3-carboxylate by thin-layer chromatographic comparison on silica gel with the product of Example 5.

EXAMPLE 10

4-Nitrobenzyl(3R,5R,Z)-2-[2-(pyrid-4-yl thio)ethylidene]clavam-3-carboxylate

4-Nitrobenzyl (3R,5R,Z)-2-(2-chloroethylidene)-clavam-3-carboxylate (350 mg.) was added to a stirred solution of 4-mercaptopyridine (250 mg.) and sodium iodide (150 mg.) in N,N-dimethylformamide (10 ml) containing pyridine (0.016 ml.). The resulting solution was stirred at room temperature for 15 minutes, during which time the solution became cloudy. The mixture was partitioned between ethyl acetate (150 ml) and water (100 ml). The organic phase was washed with water (3×50 ml) and saturated brine (20 ml), dried over sodium sulphate, treated with charcoal, filtered through Kieselguhr, and concentrated in vacuo to give title compound as a fawn gum (202 mg.), with n.m.r. spectrum and chromatographic characteristics similar to those of the Z-isomer described in Example 5.

EXAMPLE 11

4-Nitrobenzyl(3R,5R,E)-2-(2-chloroethylidene)clavam-3-carboxylate

A solution of 4-nitrobenzyl(3R,5R,Z)-2-(2-hydroxyethylidene)clavam-3-carboxylate (10.0 g) in dry tetrahydrofuran (100 ml.) and pyridine (3.2 ml) was stirred at −20° and treated with a solution of thionyl chloride (2.6 ml) in diethylether (20 ml). After a temperature rise to +5°, the resulting white suspension was cooled to −10° and then stirred at −10°–0° for 5 minutes. The reaction mixture was then diluted with ether (2 liters) and washed successively with water (3×) and saturated aqueous sodium hydrogen carbonate (2×). The ether layer was dried and concentrated to give a slurry (volume ca. 200 ml) of colourless crystals which were collected by filtration, washed with ether and dried in vacuo to afford 4-nitrobenzyl(3R,5R,Z)-2-(2-chloroethylidene)clavam-3-carboxylate (4.6 g). The filtrate and ether washings were concentrated to ca. 50 ml and the resulting crop of colourless crystals was collected by filtration, washed with ether, and dried in vacuo to afford the title ester (0.806 g), $\lambda_{max}^{EtOH}$ 363.5 nm ($\epsilon$ 10,400) $\lambda_{max}$ (Nujol) 1800 ($\beta$-lactam), 1740 (ester), 1682 (O—C=C), 1516 and 1340 cm$^{-1}$ (NO$_2$), $\tau$ (CD$_3$)$_2$CO 1.80, 2.32 (ABq, J 8 Hz, aromatic protons), 4.2 (d, J 2 Hz, C-5H), 4.40 (s, C-3H), 4.62 (s, benzyl protons), 4.72 (t, J 8 Hz, =CH—), 5.76 (d, J 8 Hz, CH$_2$Cl 6.36 (dd, J 16 and 2 Hz, C-6$\alpha$H) and 6.92 (d, J 16 Hz, C-6$\beta$H).

We claim:

1. A compound of the formula (II)

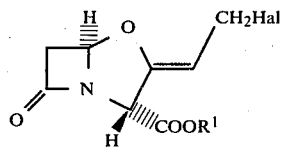

(II)

wherein Hal represents a chlorine, bromine or iodine atom and $R^1$ is selected from the group consisting of alkyl and alkenyl of up to 8 carbon atoms; alkyl and alkenyl of up to 8 carbon atoms having a substituent selected from the group consisting of methoxy, fluoro, chloro, bromo, iodo, cyano, acetoxy, pivaloyloxy, p-bromobenzoyl and carboethoxy; phenyl; benzyl; phenyl or benzyl having a substituted selected from the group consisting of chloro, o-nitro, p-nitro, cyano, p-methyl and p-methoxy; diphenylmethyl; triphenylmethyl; fur-2-ylmethyl; thien-2-ylmethyl; pyrid-4-ylmethyl; fur-2-ylmethyl, thien-2-ylmethyl or pyrid-4-ylmethyl substituted by lower alkyl on the heterocyclic group; a cycloalkyl group containing up to 12 carbon atoms; tetrahydropyranyl; phthalidyl; and a stannyl group, the tin atom having three substituents selected from the group consisting of C$_{1-4}$ alkyl, phenyl, benzyl, phenyloxy and benzyloxy; or the E-isomer thereof.

2. The compound of claim 1 wherein $R^1$ represents mono-(monocyclicaryl)alkyl substituted by a group selected from the group consisting of o-nitro, p-nitro, sulphonyl, p-methoxy and p-methyl groups.

3. The compound of claim 1 wherein $R^1$ represents a p-nitrobenzyl, diphenylmethyl or benzyl group.

4. The compound of claim 3 wherein Hal represents a chlorine or bromine atom.

5. p-Nitrobenzyl-(3R,5R,Z)-2-(2-bromethylidene)-clavam-3-carboxylate.

6. p-Nitrobenzyl-(3R,5R,Z)-2-(2-chloroethylidene)-clavam-3-carboxylate.

* * * * *